United States Patent [19]

Wittig et al.

[11] Patent Number: 5,606,139
[45] Date of Patent: Feb. 25, 1997

[54] SOIL SAMPLE PROBE WITH RETAINING RING FOR HOLDING CORE-CATCHING STRUCTURE WITHIN THE PROBE

[75] Inventors: Volker Wittig, Salina; Melvin P. Kejr, Brookville; Thomas M. Christy, Salina, all of Kans.

[73] Assignee: Kejr Engineering, Inc., Salina, Kans.

[21] Appl. No.: 433,874

[22] Filed: May 2, 1995

[51] Int. Cl.$^6$ ........................................ G01N 1/04
[52] U.S. Cl. ............................ 73/864.44; 73/864.45
[58] Field of Search ........................ 73/864.44, 864.45, 73/864.63, 864.14, 863.84

[56] References Cited

U.S. PATENT DOCUMENTS

| | | | |
|---|---|---|---|
| 2,378,484 | 6/1945 | Johnston et al. | 73/864.44 |
| 5,186,263 | 2/1993 | Kejr et al. | 175/20 |
| 5,417,122 | 5/1995 | Casey et al. | 73/864.44 |
| 5,419,211 | 5/1995 | Rodel et al. | 73/864.45 |

FOREIGN PATENT DOCUMENTS

| | | | |
|---|---|---|---|
| 404174189 | 6/1992 | Japan | 73/864.44 |
| 1046420 | 10/1983 | U.S.S.R. | 73/864.44 |

OTHER PUBLICATIONS

Geoprobe Systems 1993–1994 Equipment and Tools Catalog, pp. 4.1 to 4.16. (1994).

*Primary Examiner*—Richard Chilcot
*Assistant Examiner*—Max H. Noori
*Attorney, Agent, or Firm*—Shook, Hardy & Bacon L.L.P.

[57] ABSTRACT

A soil probe includes an annular cutting shoe for directing soil into the probe. The cutting shoe has a connecting flange with the groove formed on its outer surface. A sample tube is removably attached at its lower end to the cutting shoe and is adopted to be removably attached at its upper end to the end of a probe rod string. The retainer has an inner surface with a lip formed thereon for engaging the groove of the connecting flange. The lip is securely maintained in the groove by the positioning of the retainer between the inner surface of the sample tube and the outer surface of the connecting flange. A liner is positioned inside of the sample tube for receiving a soil sample. The liner and the retainer are connected together so that the retainer limits buckling of the liner during sampling due to the engagement of soil being sampled with the interior surface of the liner.

18 Claims, 2 Drawing Sheets

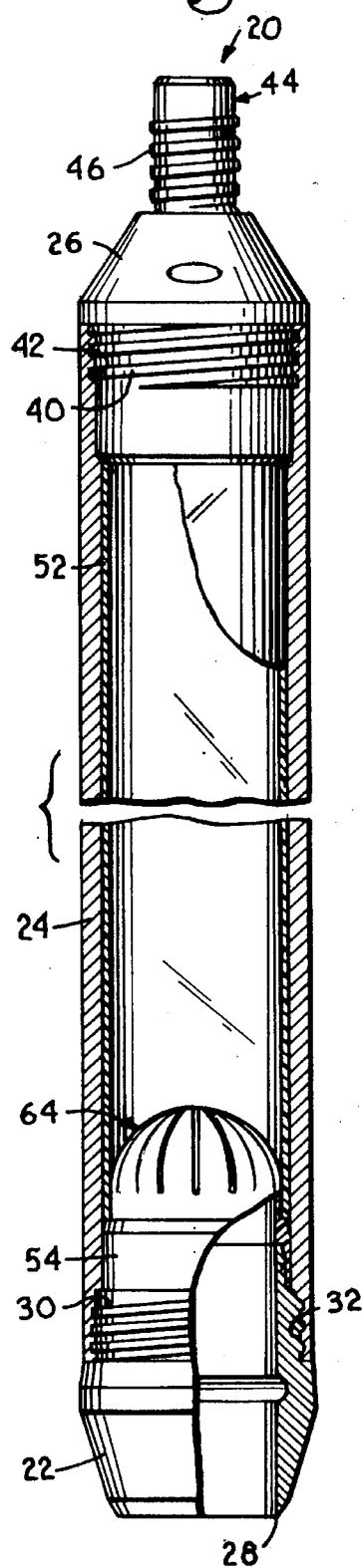
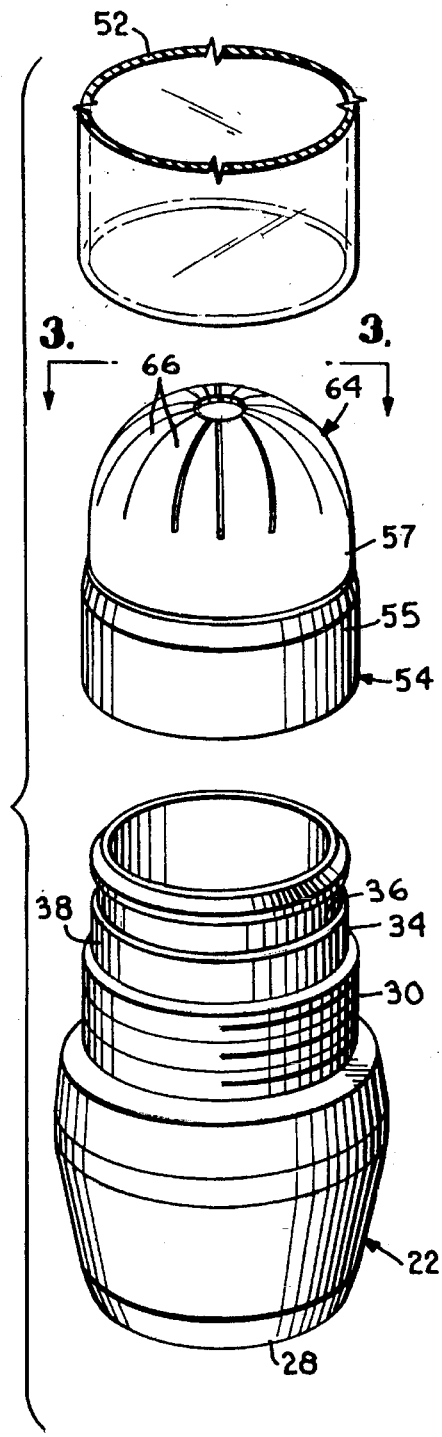
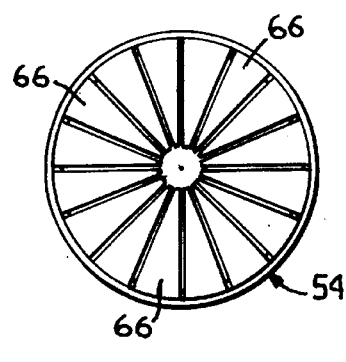
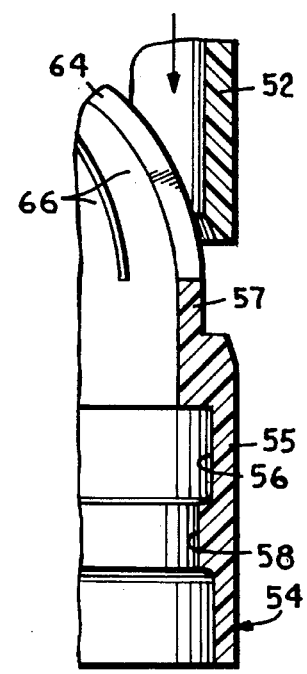

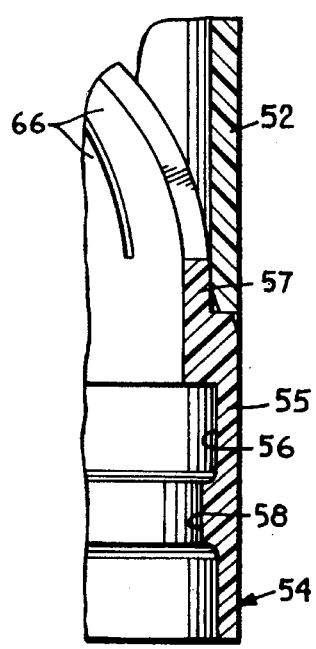
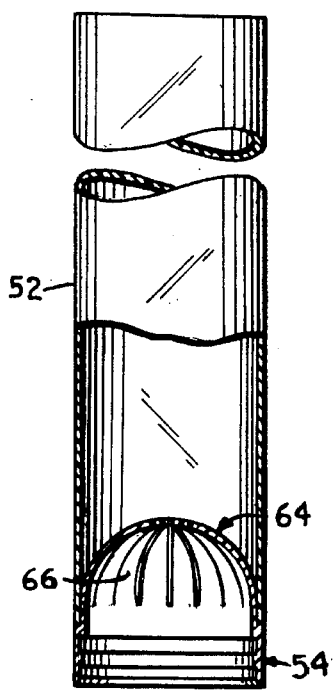
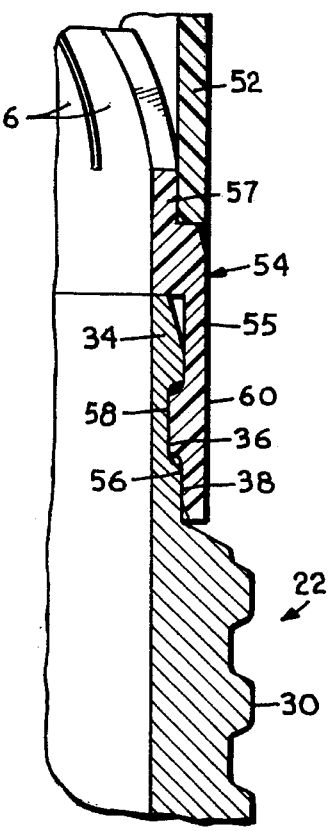
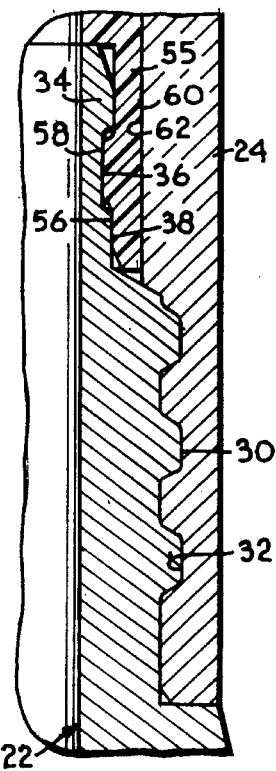
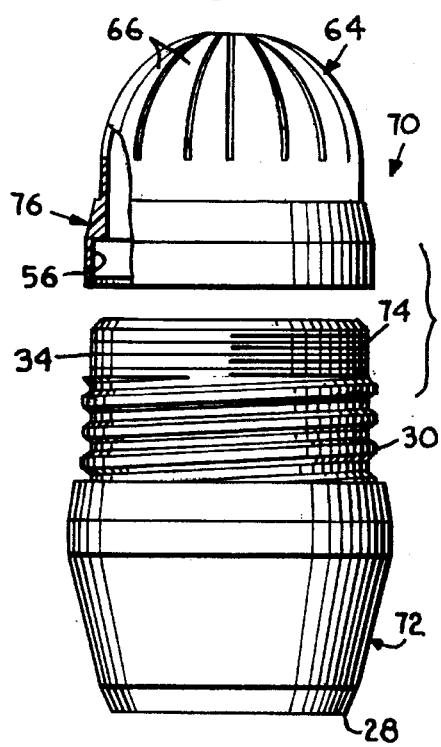
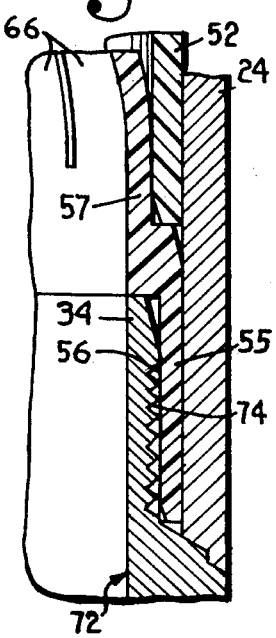

SOIL SAMPLE PROBE WITH RETAINING RING FOR HOLDING CORE-CATCHING STRUCTURE WITHIN THE PROBE

This invention relates to probes for obtaining soil samples below the surface of the ground.

For many years, soil samples have been obtained to determine soil conditions prior to construction of structures on the ground and to locate certain mineral deposits. Furthermore, these samples may be used for studying chemical dissipation and residue, for determining the concentration of environmental contaminants, for investigating hazardous waste sites and for other uses well-known in the art.

Recently, probing systems which utilize a percussion hammer have been used to drive a soil sample probe into the ground. One such system involves continuous sampling from the ground surface downward to a particular depth. This sampling system utilizes a cylindrical sample tube having a cutting shoe for directing soil into the sample tube disposed on one end and a drive head for connection to a probe rod string disposed on the other end. In order to take the first soil sample adjacent the surface, the sample tube is driven its full length into the ground, thus collecting a first core soil sample within the tube. The sample tube is then removed from the ground and the soil sample therein removed.

The sample tube may then be lowered into the previously sampled hole and the next sampling interval taken at the lower depth. In order to transmit the percussive forces from the hammer to the sampling tube at this lower depth, probe rods are attached to the upper end of the probe. Additional sampling intervals at deeper depths can be taken in like manner.

Another type of soil sample probe is driven into the ground to a desired depth without collecting a sample, and thereafter a sample taken at that depth. One such probe is described in U.S. Pat. No. 5,186,263 which is hereby incorporated herein by reference. The probe disclosed in this patent utilizes a releasable drive point telescopically received within the cutting shoe. The probe of the patent is driven to a particular depth with the sample tube completely sealed from the surrounding soil. After a desired depth is reached, the drive point is released from its fixed position by using a string of extension rods extending through the aligned bores of the probe rod string. The probe is then further driven into the ground to collect the sample. As the probe is further driven, the released drive point moves relatively upwardly into the sample tube by the downward movement of the sample tube to collect the soil sample core. After the soil sample tube is full, the probe is extracted from the ground.

Oftentimes, a sample tube liner is used with a soil sample probe whether it be of a continuous sampling type or a releasable drive point type. These liners typically are a clear plastic cylinder received within the sample tube. The soil sample is guided into the liner by the cutting shoe. The liner allows easy removal and storage of the soil sample core. Further, if a clear plastic liner is utilized, the different strata of the soil sample can be easily inspected while still in the liner and the relative positions of the strata are preserved.

The lower end of a plastic liner typically is force-fitted over an annular connecting flange of the cutting shoe. The liner with the cutting shoe on its lower end is then telescopically received within the sampling tube and the cutting shoe screwed into place on the lower end of the sample tube.

Various problems can result from the use of liners. More specifically, as a soil sample is moved upwardly into the liner by the downward movement of the tube and liner under the percussive action of the hammer, the sample tends to grip the inner surface of the liner. This frictional engagement between the sample and the liner oftentimes results in disconnection of the liner from the connecting flange of the cutting shoe and buckling of the liner within the soil sample tube. Certain soil types tend to magnify the frictional engagement between the soil sample and the liner, and thus increase the possibility of buckling. For example, some types of clay expand when compressed within the liner, thus increasing frictional engagement with the inner wall of the liner. Further, particular types of dense sand have angular particles which tend to grab the inner surface of the liner.

In order to alleviate this buckling problem, metal liners made of brass or stainless steel have sometimes been used. However, such liners typically are more expensive and more difficult to manufacture than plastic liners. Further, metal liners do not offer the ability to see the core sample within the liner as do clear plastic liners.

During the collection of sandy soil, which sometimes lacks substantial cohesion, it may be difficult to keep the sample from exiting the open end of the sample tube during extraction of the probe from the ground. In order to alleviate this problem and hold the soil sample within the sample tube, prior art structures have utilized a basket-type device at the lower end of the tube. Such devices allow a soil sample to pass into the sample tube but inhibit soil from passing back out of the sample tube.

One such device is manufactured by Diedrich Drill, Inc. of La Porte, Indiana. This device includes a thick rigid ring having a plurality of inwardly and upwardly extending curved flexible fingers. The device is typically positioned within the cutting shoe. The flexible fingers deflect outwardly and allow soil to pass into the sample tube. The rigid ring is necessary to ensure that, as the soil passes through the device, the device is not carried along with the soil into the sample tube. More specifically, the ring engages the bottom edge of the sample tube to prevent upward movement of the device, and thus must have sufficient rigidity and strength to prevent its deformation when subjected to the force of soil passing therethrough.

This type of device with its rigid ring base is disadvantageous for various reasons. The rigid ring may interfere with the flow of the soil sample into the sampling tube because, in order to ensure the ring is rigid enough and will not deform, the inner diameter of the ring may be smaller than the inner diameter of the cutting shoe and/or the sample tube. Further, in order to accommodate the relatively substantial size of the rigid ring, the cutting shoe and/or sample tube must have a correspondingly large slot or space. The slot or space decreases the wall thickness of the shoe or tube, thus decreasing its strength.

Therefore, a novel probe construction is needed to alleviate the problems associated with prior art probe constructions.

Accordingly, it is a primary object of this invention to provide a soil sampling probe which is constructed to decrease the possibility of buckling of a sample tube liner due to the frictional engagement between the soil sample and the liner during driving of the probe.

A further important object of this invention is to provide a probe construction wherein a core catching device, which prevents soil from exiting the sample tube once it is collected, is securely held in place adjacent the cutting shoe during sampling without the need for a dense rigid structure.

A still further object of this invention is to provide a probe construction wherein the liner and the catching device are held in place by a relatively thin-walled retainer which engages a connecting flange of the cutting shoe and is securely maintained in engagement by the confinement of the retainer between the sample tube and the connecting flange.

Another object of this invention is to provide a probe construction which allows use of a sample tube liner that is made of a material that is less expensive than, easier to manufacture than, lighter than, and less rigid than a metal liner while at the same time being resistant to buckling.

These and other and important aims and objectives of the present invention will be further described, or will become apparent from the following description and explanation of the drawings, wherein:

FIG. 1 is a fragmentary, detailed cross-sectional view of a soil sample probe embodying the principals of this invention, parts being broken away and show in cross-section to reveal details of construction;

FIG. 2 is an enlarged, exploded, perspective view of the cutting shoe, retainer, and liner of the probe construction shown in FIG. 1;

FIG. 3 is a plan view taken generally along line 3—3 of FIG. 2 and showing the core catching basket of the retainer;

FIG. 4 is a fragmentary enlarged detailed cross-sectional view of the probe showing the step of positioning the liner around the retainer so that the liner can be attached thereto;

FIG. 5 is a view similar to FIG. 4 but showing the liner attached to the retainer;

FIG. 6 is a fragmentary elevational view of the combined liner and retainer, parts being broken away and shown in cross-section to reveal details of construction;

FIG. 7 is a fragmentary enlarged detailed cross-sectional view of the probe showing the step of attaching the retainer to the cutting shoe so that the lip of the retainer is received in the groove of the cutting shoe;

FIG. 8 is a view similar to FIG. 7 showing the sample tube attached to the cutting shoe so that the retainer is confined between the cutting shoe and the sample tube to securely maintain the lip of the retainer in the groove of the cutting shoe;

FIG. 9 is an exploded, elevational view of the retainer and cutting shoe of an alternative construction, parts being broken away and shown in cross-section to reveal details of construction; and FIG. 10 is a fragmentary enlarged detailed cross-sectional view showing the retainer connecting arrangement of the alternative construction shown in FIG. 9 with the retainer confined between the cutting shoe and the sample tube to secure the connection of the retainer to the cutting shoe.

A soil sample probe embodying the principals of this invention is broadly designated in the drawings by the reference numeral 20. Probe 20 includes an annular cutting shoe 22, a cylindrical sample tube 24, and a drive head 26 as best shown in FIG. 1.

With reference to FIG. 2, cutting shoe 22 has an annular, sharpened edge 28 for cutting through the soil and for directing a soil sample into tube 24. Shoe 22 further has a male thread surface 30 for engaging a female thread surface 32 located on the lower end of tube 24 so that shoe 22 can be removably attached to tube 24. Shoe 22 further has an annular connecting flange 34 with an annular groove 36 formed on its outer surface 38.

Drive head 26 is removably attached to the upper end of tube 24 by the engagement of a male thread surface 40 of head 26 with a female thread surface 42 of tube 24. Head 26 has a reduced diameter connecting portion 44 with a male thread surface 46 formed on its outer surface. Portion 44 can be used to connect the probe to the bottom of a string of probe rods (not shown) by engaging the surface 46 with a female thread surface of the directly adjacent probe rod (not shown). Further, a drive cap (not shown) can be positioned on connecting portion 44 to initially drive the probe into the ground, as will be more fully described.

A cylindrical liner 52 is telescopically received inside of sample tube 24, as best shown in FIG. 1. Liner 52 is preferably made of a clear plastic material, such as PETG. Further, liner 52 can also be made of Teflon if it is not necessary to maintain visibility though the wall of the liner. The lower end of liner 52 is attached to a ring-shaped retainer 54, as best shown in FIGS. 4–7. Retainer 54 has a thin walled section 55 and an attaching section 57, as shown in FIGS. 2 and 4. The lower end of liner 52 is attached to section 57. Retainer 54 is preferably made of a plastic material so that liner 52 can be heat-welded thereto.

Retainer 54 has an inner surface 56 from which projects an annular lip 58, as shown in FIGS. 4 and 5. Retainer 54 receives flange 34 of shoe 22 so that lip 58 is positioned in groove 36 and surface 56 of the retainer lies adjacent surface 38 of the flange, as best shown in FIGS. 7 and 8. The outer surface 60 of the retainer lies adjacent the inner surface 62 of the tube 24. This confinement or "sandwiching" of the thin wall 55 of the retainer between tube 24 and flange 34 ensures that lip 58 remains securely within groove 36, and thus, that the lower end of the liner remains attached to the cutting shoe during driving to prevent buckling of the liner. The confinement arrangement allows the retainer to have a relatively thin walled, nonrigid construction. This arrangement utilizes the shear strength of the material out of which the retainer is made to sustain a secure connection between the retainer and the connecting flange.

Retainer 54 can have a core-catching assembly or basket 64 as best shown in FIGS. 1–3. Basket 64 is comprised of a plurality of flexible arcuate-shaped fingers 66. Fingers 66 can be formed integrally with the retainer and project upwardly and inwardly therefrom as depicted in the figures. Further, fingers 66 can be connected to the retainer by any suitable means. Fingers 66 deflect outwardly toward the inner surface of liner 52 as soil is forced into the liner by the driving of the probe into the ground. After tube 24 and liner 52 have been filled with a soil sample and the probe is pulled upwardly to remove the sample, fingers 66 will resume their undeflected original positions. Thus, during extraction of the probe from the ground, the fingers in their original undeflected positions will inhibit soil collected in the liner from escaping through the lower portion of the liner and out of the cutting shoe. As is apparent, basket 64 is only needed when sandy or loose soil is sampled. When compressed dense soil is sampled, a retainer without a basket 64 can be used.

With reference to FIGS. 4–6, the liner and the retainer are preferably attached to one another at the manufacturing facility and marketed as a single unit for field use. Probe 20 is assembled in the field by first positioning retainer 54 with the liner attached thereto around flange 34 of shoe 22 so that lip 58 is disposed in groove 36 as shown in FIG. 7. The combined structure of the cutting shoe and the liner is then telescopically received in sample tube 24 and the shoe rotated so that thread surfaces 30 and 32 mate as shown in FIGS. 1 and 8. The drive head 26 is connected to the upper end of the sample tube by engaging the thread surfaces 40 and 42. The probe is then ready to be driven into the ground.

In operation, for continuous sampling, the probe is driven into the ground by a hydraulic percussion hammer (not shown). A drive cap typically is connected to portion 44 of head 26 and serves as the structure upon which the percussive forces of the hammer are applied. The first sample interval extends from the ground surface to a depth equal to the approximate length of the probe, which is typically 46 inches. As a soil sample frictionally engages the interior surface of the liner during the percussive driving of the probe into the ground, the liner is firmly held at its lower end to the cutting shoe by the engagement of lip 58 with groove 36 to thus inhibit upward movement or buckling of the liner.

Additionally, if a basket 64 is used, the basket is held firmly at the lower end of the sample tube due to the basket's integral formation with the retainer. More specifically, the attachment of the retainer to the cutting shoe and the integral formation of the basket with the retainer ensures that, when soil passes through and frictionally engages the fingers of the basket, the basket does not deform and inadvertently travel upwardly with the sample. Thus, the basket is held in place by the relatively thin-walled relatively flexible retainer as opposed to a thick-walled rigid structure.

After the sample tube has been filled with the soil sample, it is removed from the ground utilizing a pull cap attached to its upper end as it well-known in the art. After the probe is removed from the ground, the liner with the sample therein is removed from the sample tube and disengaged from the cutting shoe. The ends of the liner can be sealed off to maintain the core sample with its different strata at their relative locations. Further, because the liner is preferably made of a clear material, the sample can be easily inspected. If desired, the soil sample can be removed from the liner by forcing the core out of the liner or by simply slitting the liner and peeling it from the core.

In order to take a soil sample at the next interval down from the initial sample, the probe is reassembled with a new liner and retainer and lowered into the sample hole utilizing probe rods attached to the drive head of the probe. After the probe engages the unsampled interval, percussive driving forces are applied to the probe from the hammer via the probe rod string. After the second sample is taken, the probe is retrieved and the core removed in the same manner as described with regard to the first sample. Additional samples can be taken in the same manner.

In addition to use with a continuous sampling system, the retainer 54, liner 52 and basket 64 can be used with a probe having a releasable drive point. Such a probe is driven into the ground to a desired depth, and thereafter a sample taken at that depth. In this type of probe, the drive point is telescopically received and held within the cutting shoe during driving of the probe to the desired depth. The drive point is then released from its position so that it moves relatively upwardly within the liner and sample tube as the soil sample is taken. If a basket 64 is used in such a releasable drive point probe, the fingers 66 of the basket deflect outwardly to allow the drive point to pass through the basket. The retainer is connected to the cutting shoe and confined between the connecting flange of the cutting shoe and the sample tube in the same manner as described above to inhibit buckling of the liner and prevent inadvertent upward movement of the basket.

As an alternative to forming the retainer and liner separately and thereafter connecting the structures, the liner and retainer can be integrally formed as one piece. Furthermore, because retainer 54 is used to securely hold the lower end of the liner adjacent the cutting shoe, an extremely flexible fabric-like liner may be used which does not maintain a cylindrical shape when not filled with a sample.

Further, in some soil conditions, for instance, chemically contaminated soil, it may be preferable to use a metal liner as opposed to a plastic liner. If a metal liner is used, the liner normally will not suffer the buckling problems of the plastic liner due to the strength and rigidity of the metal liner. However, if a core-catching basket is required for loose soil, there is still a need to maintain the basket at its position adjacent the cutting shoe of the probe. Therefore, a retainer with a basket as described above that is connected to the cutting shoe in the manner described above can be used to maintain the basket at its relative position. The metal liner utilized would not be attached to the retainer, but simply would fit around the basket and the connecting section of the retainer.

With reference to FIGS. 9 and 10, an alternative construction 70 is shown. In FIGS. 9 and 10, like reference numerals are used to indicate parts similar or identical to those in FIGS. 1–8. Alternative cutting shoe 72 is similar to cutting shoe 22, except that shoe 72 has a thread gripping surface 74 formed on its connecting flange 34 instead of a groove 36 formed thereon.

Alternate retainer 76 is also similar to retainer 54, except that retainer 76 does not have lip 58 extending from its inner surface 56. Surface 56 of retainer 76 engages gripping surface 74 of shoe 72, but does not have a preformed thread surface thereon. The pliable plastic material out of which retainer 76 is made is deformed by gripping surface 74 as the retainer is threaded thereon. Thus, although surface 56 does not have preformed threads, it deforms to engage the gripping surface 74 as the retainer is fitted over and rotated onto the connecting flange of shoe 72. As with retainer 54, the wall 55 of retainer 76 is confined between connecting flange 34 and the inner surface of the sample tube. This confining arrangement ensures that gripping surface 74 adequately engages surface 56 of the retainer to securely hold the retainer to the connecting flange. As with retainer 54, liner 52 can be attached to the connecting section of retainer 76, thus inhibiting buckling of the liner.

Retainer 76 can also have a core-catching basket 64 formed integrally therewith. Thus, because retainer 76 is securely held in position adjacent the cutting shoe, so is basket 64. As with retainer 22, retainer 76 also utilizes a relatively thin walled structure to prevent inadvertent migration of the basket 64 into the sample tube. As with probe construction 20, liner 52 can either be attached to retainer 76 by any suitable means, for example, heat welding, or can be formed integrally with the retainer. Retainer 76 can also be used with a metal liner, in which case the liner is not attached to the retainer but simply fitted over the connecting section of the retainer.

Having described the invention what is claimed:

1. A soil sampling probe adapted to be driven into the ground on the lower end of a probe rod string, comprising:

an annular cutting shoe for directing soil into the probe, said cutting shoe having a connecting flange with a groove formed on its outer surface;

a sample tube removably attached at is lower end to said cutting shoe and adapted to be removably attached at its upper end to the lower end of a probe rod string;

a retainer having an inner surface and an outer surface, said inner surface having a lip formed thereon, said lip positioned for engagement with said groove of said connecting flange, wherein said lip is securely maintained in said groove by the positioning of said retainer between the inner surface of said sample tube and the outer surface of said connecting flange; and a liner positioned inside of said sample tube for receiving a soil sample, said liner having an inner surface, said liner inner surface engaging at least a portion of said retainer outer surface in an overlapping relationship so that buckling of said liner due to soil being introduced into the interior of said liner is reduced.

2. The probe of claim 1 wherein said retainer is annular in shape, said retainer fitting over and surrounding said connecting flange.

3. The probe of claim 1 wherein said liner and said retainer are both made of a plastic material.

4. The probe of claim 3 wherein said retainer and said liner are heat welded together.

5. The probe of claim 1 wherein said retainer and said liner are integrally formed together.

6. The probe of claim 1 wherein said retainer has a catching means for allowing soil to pass into said sample tube and for holding the soil therein.

7. The probe of claim 6 wherein said catching means includes a plurality of inwardly and upwardly extending arcuate flexible fingers which deflect outwardly to allow soil to pass and inhibit the soil from passing back out of said tube.

8. The probe of claim 1 wherein said tube is made of a flexible fabric.

9. A soil sampling probe adapted to be driven into the ground on the lower end of a probe rod string, comprising:

an annular cutting shoe for directing soil into the probe, said cutting shoe having a connecting flange with a groove formed on its outer surface;

a sample tube removably attached at is lower end to said cutting shoe and adapted to be removably attached at its upper end to the lower end of a probe rod string; and a retainer having an inner surface, said inner surface having a lip formed thereon, said lip positioned for engagement with said groove of said connecting flange, wherein said lip is securely maintained in said groove by the positioning of said retainer between the inner surface of said sample tube and the outer surface of said connecting flange, and wherein said retainer includes a catching means for allowing soil to pass into said sample tube and holding the soil therein.

10. The probe of claim 9 wherein said catching means includes a plurality of inwardly and upwardly extending arcuate flexible fingers which deflect outwardly to allow soil to pass into said sample tube and inhibit the soil from passing back out of said tube.

11. The probe of claim 9 wherein said retainer is annular in shape, said retainer fitting over and surrounding said connecting flange.

12. A soil sampling probe adapted to be driven into the ground on the lower end of a probe rod string, comprising:

an annular cutting shoe for directing soil into the probe, said cutting shoe having a connecting flange;

a sample tube removably attached at is lower end to said cutting shoe and adapted to be removably attached at its upper end to the lower end of a probe rod string; and a retainer having an inner surface, said connecting flange having gripping means for engaging said inner surface of said retainer, wherein the effectiveness of said gripping means is increased by the positioning of said retainer between the inner surface of said sample tube and the outer surface of said connecting flange, said retainer further including catching means for allowing soil to pass into said sample tube and for holding the soil therein.

13. The probe of claim 12 wherein said griping means includes a threaded surface formed on the exterior surface of said connecting flange, said threaded surface gripping and engaging the inner surface of said retainer.

14. The probe of claim 12 wherein said retainer is annular in shape, said retainer fitting over and surrounding said connecting flange.

15. The probe of claim 12 further comprising:

a liner positioned inside of said sample tube for receiving a soil sample, said liner and said retainer being connected together so that said retainer holds the lower edge of said liner to resist buckling due to soil being introduced into the interior of said liner.

16. The probe of claim 15 wherein said liner and said retainer are both made of a plastic material.

17. The probe of claim 16 wherein said retainer and said liner are heat welded together.

18. The probe of claim 15 wherein said retainer and said liner are integrally formed together.

* * * * *